(12) United States Patent
Stone et al.

(10) Patent No.: US 9,271,879 B2
(45) Date of Patent: Mar. 1, 2016

(54) ARTICLE HAVING A SEAL AND PROCESS FOR FORMING THE SAME

(75) Inventors: Keith Joseph Stone, Fairfield, OH (US); Roger Dale Young, Ft. Mitchell, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 771 days.

(21) Appl. No.: 12/721,905

(22) Filed: Mar. 11, 2010

(65) Prior Publication Data
US 2010/0233428 A1  Sep. 16, 2010

Related U.S. Application Data

(60) Provisional application No. 61/159,906, filed on Mar. 13, 2009.

(51) Int. Cl.
*B32B 3/24* (2006.01)
*B32B 3/28* (2006.01)
(Continued)

(52) U.S. Cl.
CPC ............ *A61F 13/15739* (2013.01); *B26F 1/26* (2013.01); *B29C 59/022* (2013.01); *B29C 65/56* (2013.01); *B29C 65/76* (2013.01); *B29C 66/21* (2013.01); *B29C 66/45* (2013.01); *B29C 66/81264* (2013.01); *B29C 66/81423* (2013.01); *B29C 66/81433* (2013.01); *B29C 66/83413* (2013.01); *B29C 66/91411* (2013.01); *B29C 66/91935* (2013.01); *B32B 3/263* (2013.01); *B32B 3/266* (2013.01); *B32B 3/28* (2013.01); *B32B 3/30* (2013.01); *B32B 7/02* (2013.01); *B32B 7/045* (2013.01); *B32B 27/20* (2013.01); *B32B 38/06* (2013.01); *B29C 59/04* (2013.01); *B29C 59/06* (2013.01); *B29C 65/70* (2013.01); *B29C 65/72* (2013.01); *B29C 66/729* (2013.01); *B29C 66/919* (2013.01); *B29C 66/9121* (2013.01); *B29C 66/9161* (2013.01); *B29C 66/91216* (2013.01); *B29K 2995/007* (2013.01); *B29K 2995/0089* (2013.01); *B31F 2201/0733* (2013.01); *B31F 2201/0738* (2013.01); *B32B 7/04* (2013.01); *B32B 7/08* (2013.01); *B32B 27/08* (2013.01); *B32B 38/12* (2013.01); *B32B 2037/0092* (2013.01); *B32B 2323/04* (2013.01); *B32B 2323/10* (2013.01);
(Continued)

(58) Field of Classification Search
None
See application file for complete search history.

(56) References Cited

U.S. PATENT DOCUMENTS

| 2,012,405 | A | * | 8/1935 | Salfisberg | ............... | 206/232 |
|---|---|---|---|---|---|---|
| 2,549,069 | A | * | 4/1951 | Donofrio | ............... | 206/484 |

(Continued)

FOREIGN PATENT DOCUMENTS

| DE | 3439555 A1 | 4/1986 |
|---|---|---|
| EP | 0598970 A1 | 6/1994 |

(Continued)

OTHER PUBLICATIONS

Machine Translation of JP 2007167416 A, Jul. 2007.*
(Continued)

*Primary Examiner* — Jeff Vonch
(74) *Attorney, Agent, or Firm* — Andrew J. Hagerty

(57) ABSTRACT

An article having an embossed seal includes at least two webs, and an embossed seal joining a portion of the at least two webs, the seal including co-registered concentric discrete extended elements formed in the at least two webs, the discrete extended elements having open proximal ends.

11 Claims, 8 Drawing Sheets

(51) Int. Cl.
*B32B 7/04* (2006.01)
*B32B 7/08* (2006.01)
*B32B 27/08* (2006.01)
*B32B 38/06* (2006.01)
*B29C 65/56* (2006.01)
*B29C 65/76* (2006.01)
*A61F 13/15* (2006.01)
*B32B 3/30* (2006.01)
*B32B 3/26* (2006.01)
*B26F 1/26* (2006.01)
*B29C 59/02* (2006.01)
*B29C 65/00* (2006.01)
*B32B 7/02* (2006.01)
*B32B 27/20* (2006.01)
*B32B 37/10* (2006.01)
*B32B 37/30* (2006.01)
*B29C 65/70* (2006.01)
*B29C 65/72* (2006.01)
*B32B 27/32* (2006.01)
*B29C 59/04* (2006.01)
*B29C 59/06* (2006.01)
*B32B 38/12* (2006.01)
*B32B 37/00* (2006.01)

(52) U.S. Cl.
CPC ... *Y10T 156/1039* (2015.01); *Y10T 428/24289* (2015.01); *Y10T 428/24496* (2015.01); *Y10T 428/24521* (2015.01); *Y10T 428/24545* (2015.01)

(56) References Cited

U.S. PATENT DOCUMENTS

| | | | |
|---|---|---|---|
| 2,557,794 A * | 6/1951 | Charles | 206/484 |
| 2,685,911 A * | 8/1954 | Haller | 428/184 |
| 3,033,723 A * | 5/1962 | Mead | 428/166 |
| 3,086,899 A * | 4/1963 | Ingraham et al. | 428/158 |
| 3,466,212 A * | 9/1969 | Clayton et al. | 156/199 |
| 3,708,366 A * | 1/1973 | Donelly | 156/209 |
| 3,719,736 A | 3/1973 | Woodruff | |
| 3,779,285 A | 12/1973 | Sinibaldo | |
| 3,857,144 A * | 12/1974 | Bustin | 156/209 |
| 3,899,805 A * | 8/1975 | McMillan | 24/584.1 |
| 3,911,187 A | 10/1975 | Raley | |
| 3,940,529 A * | 2/1976 | Hepford et al. | 428/178 |
| 4,211,743 A | 7/1980 | Nauta et al. | |
| 4,319,868 A | 3/1982 | Riemersma et al. | |
| 4,343,848 A | 8/1982 | Leonard, Jr. | |
| 4,518,643 A * | 5/1985 | Francis | 428/131 |
| 4,546,029 A | 10/1985 | Cancio et al. | |
| 4,578,068 A | 3/1986 | Kramer et al. | |
| 4,695,422 A | 9/1987 | Curro et al. | |
| 4,778,644 A | 10/1988 | Curro et al. | |
| 4,995,930 A | 2/1991 | Merz et al. | |
| 5,143,774 A | 9/1992 | Cancio et al. | |
| 5,157,901 A * | 10/1992 | Okamoto et al. | 53/478 |
| 5,158,819 A | 10/1992 | Goodman et al. | |
| 5,180,620 A * | 1/1993 | Mende | 428/138 |
| 5,181,610 A * | 1/1993 | Quick et al. | 206/447 |
| 5,221,276 A * | 6/1993 | Battrell | 604/389 |
| 5,281,371 A | 1/1994 | Tamura et al. | |
| 5,324,279 A * | 6/1994 | Lancaster et al. | 604/391 |
| 5,331,791 A * | 7/1994 | Fux et al. | 53/478 |
| 5,635,276 A * | 6/1997 | Biagioli et al. | 428/132 |
| 5,650,215 A | 7/1997 | Mazurek et al. | |
| 5,670,110 A | 9/1997 | Dirk et al. | |
| 5,846,636 A | 12/1998 | Ruppel et al. | |
| 5,858,515 A | 1/1999 | Stokes et al. | |
| 5,945,196 A | 8/1999 | Rieker et al. | |
| 5,972,280 A | 10/1999 | Hoagland | |
| 6,045,894 A | 4/2000 | Jonza et al. | |
| H1927 H | 12/2000 | Chen et al. | |
| 6,242,074 B1 | 6/2001 | Thomas | |
| 6,245,273 B1 | 6/2001 | Wendler, Jr. | |
| 6,368,539 B1 | 4/2002 | Greenfield et al. | |
| 6,428,209 B1 * | 8/2002 | Janssen | 383/93 |
| 6,506,473 B1 | 1/2003 | Hisanaka et al. | |
| 6,531,230 B1 | 3/2003 | Weber et al. | |
| 6,599,612 B1 | 7/2003 | Gray | |
| 6,719,742 B1 | 4/2004 | McCormack et al. | |
| 6,780,372 B2 | 8/2004 | Gray | |
| 6,788,463 B2 | 9/2004 | Merrill et al. | |
| 6,797,366 B2 | 9/2004 | Hanson et al. | |
| 6,846,445 B2 | 1/2005 | Kim et al. | |
| 7,037,569 B2 | 5/2006 | Curro et al. | |
| 7,172,801 B2 | 2/2007 | Hoying et al. | |
| 7,338,038 B2 * | 3/2008 | Maurer et al. | 267/144 |
| 7,402,723 B2 | 7/2008 | Stone et al. | |
| 7,642,207 B2 | 1/2010 | Bohemer et al. | |
| 7,734,389 B2 | 6/2010 | Shin | |
| 7,799,254 B2 | 9/2010 | Harvey et al. | |
| 8,182,728 B2 | 5/2012 | Cree et al. | |
| 8,241,543 B2 | 8/2012 | O'Donnell et al. | |
| 2001/0014796 A1 | 8/2001 | Mizutani et al. | |
| 2003/0120241 A1 | 6/2003 | Sorebo et al. | |
| 2003/0187170 A1 | 10/2003 | Burmeister | |
| 2003/0228445 A1 | 12/2003 | Vaughn et al. | |
| 2004/0046290 A1 | 3/2004 | Kim et al. | |
| 2004/0119207 A1 * | 6/2004 | Stone et al. | 264/442 |
| 2004/0131820 A1 | 7/2004 | Turner et al. | |
| 2004/0209041 A1 | 10/2004 | Muth et al. | |
| 2004/0247833 A1 * | 12/2004 | Copat et al. | 428/156 |
| 2005/0019530 A1 | 1/2005 | Merrill et al. | |
| 2005/0096614 A1 | 5/2005 | Perez et al. | |
| 2005/0112338 A1 * | 5/2005 | Faulks et al. | 428/204 |
| 2005/0131370 A1 * | 6/2005 | Hantke et al. | 604/385.02 |
| 2005/0191496 A1 | 9/2005 | Gray et al. | |
| 2005/0279470 A1 | 12/2005 | Redd et al. | |
| 2006/0087053 A1 * | 4/2006 | O'Donnell et al. | 264/156 |
| 2006/0128245 A1 | 6/2006 | Muth et al. | |
| 2006/0286343 A1 | 12/2006 | Curro et al. | |
| 2007/0062658 A1 | 3/2007 | Wiwi et al. | |
| 2007/0261224 A1 | 11/2007 | McLeod | |
| 2008/0200320 A1 | 8/2008 | Buckner et al. | |
| 2008/0264275 A1 | 10/2008 | Wilhelm et al. | |
| 2009/0155540 A1 | 6/2009 | Merrill et al. | |
| 2010/0233428 A1 | 9/2010 | Stone et al. | |
| 2010/0247844 A1 | 9/2010 | Curro et al. | |
| 2011/0106036 A1 | 5/2011 | Ståhl et al. | |
| 2011/0223388 A1 | 9/2011 | Stone et al. | |
| 2012/0105957 A1 | 5/2012 | Merrill et al. | |

FOREIGN PATENT DOCUMENTS

| | | | | |
|---|---|---|---|---|
| EP | 995414 B1 | 9/2003 | | |
| GB | 1344054 A | 1/1974 | | |
| JP | 04-062055 A | 2/1992 | | |
| JP | 06155635 A * | 6/1994 | | B31B 1/64 |
| JP | 07206011 A * | 8/1995 | | B65D 33/00 |
| JP | 07206012 A * | 8/1995 | | B65D 33/00 |
| JP | 2007-167416 A | 7/2007 | | |
| JP | 2007167416 A * | 7/2007 | | |
| WO | WO 9424354 A1 | 10/1994 | | |
| WO | WO-97/13633 | 4/1997 | | |
| WO | WO2008120959 A1 | 10/2008 | | |
| WO | WO 2010055516 A1 * | 5/2010 | | B31F 1/07 |

OTHER PUBLICATIONS

English Abstract for JP 07206011 A, Aug. 1995.*
Nagarajan, Abbott, Yao; Rubber-Assisted Embossing Process; School of Polymer, Textile & Fiber Eng., Georgia Institute of Technology, Atlanta, GA 30332; ANTEC (2007) vol. 5, pp. 2921-2925, 5 pages.
Chang, Yang; Gas pressurized hot embossing for transcription of micro-features; Microsystem Technologies (2003) vol. 10, pp. 76-80, 5 pages; Springer-Verlag.
Dreuth, Heiden; Thermoplastic structuring of thin polymer films; Sensors and Actuators (1999) vol. 78, pp. 198-204, 7 pages; Institute of Applied Physics, University of Giessen, Heinrich-Buff-Ring 16 D-35392 Giessen, Germany; Elsevier Science S.A.

(56) References Cited

OTHER PUBLICATIONS

Heckele, Schomburg; Review on micro molding of thermoplastic polymers; Institute of Physics Publishing; Journal of Micromechanics and Microengineering (2004) vol. 14, No. 3, pp. R1-R14, 14 pages; IOP Publishing Ltd.

Kimerling, Liu, Kim, Yao; Rapid hot embossing of polymer microfeatures; Microsystem Technologies (2006) vol. 12, No. 8, pp. 730-735, 6 pages; School of Polymer, Textile and Fiber Eng., Georgia Institute of Technology, Atlanta GA 30332.

Nagarajan, Yao, Ellis, Azadegan; Through-Thickness Embossing Process for Fabrication of Three-Dimensional Thermoplastic Parts; School of Polymer, Textile & Fiber Eng., Georgia Institute of Technology, Atlanta GA 30332 and Delphi Research Labs, Shelby Township, Michigan 48315; Polymer Engineering and Science (2007) vol. 47, No. 12, pp. 2075-2084, 10 pages.

Rowland, King; Polymer deformation and filling modes during microembossing; Woodruff School of Mechanical Engineering, Georgia Institute of Technology, Atlanta, GA 30329-0405; Institute of Physics Publishing; Journal of Micromechanics and Microengineering (2004) vol. 14, No. 12, pp. 1625-1632, 8 pages; IOP Publishing Ltd.

Truckenmuller, Giselbrecht; Microthermoforming of flexible, not-buried hollow microstructures for chip-based life sciences applications; IEE Proceedings—Nanobiotechnology (Aug. 2004) vol. 151, No. 4, pp. 163-166; 4 pages.

Yao, Nagarajan; Cold Forging Method for Polymer Microfabrication; Department of Mechanical Engineering, Oakland University, Rochester, MI 48309; Polymer Engineering and Science (Oct. 2004) vol. 44, No. 10, pp. 1998-2004, 7 pages.

Yao, Nagarajan, Li, Yi; A Two-Station Embossing Process for Rapid Fabrication of Surface Microstructures on Thermoplastic Polymers; School of Polymer, Textile & Fiber Eng., Georgia Institute of Technology, Atlanta, GA 30332 and Department of Industrial, Welding and Systems Engineering, The Ohio State University, Columbus, OH 43210; Polymer Engineering and Science (2007) vol. 47, No. 4, pp. 530-539, 10 pages; Wiley InterScience; Society of Plastics Engineers.

Yao, Kuduva-Raman-Thanumoorthy; An enlarged process window for hot embossing; School of Polymer, Textile & Fiber Eng., Georgia Institute of Technology, Atlanta, GA 30332; Journal of Micromechanics and Microengineering (2008) vol. 18, pp. 1-7; 7 pages; IOP Publishing Ltd.

PCT International Search Report dated Aug. 6, 2010.

PCT International Search Report for 11633R dated Dec. 6, 2010, 6 pages.

* cited by examiner

ARTICLE HAVING A SEAL AND PROCESS FOR FORMING THE SAME

CROSS REFERENCE TO RELATED APPLICATION

This application claims the benefit of U.S. Provisional Application No. 61/159,906, filed Mar. 13, 2009.

FIELD OF THE INVENTION

The invention relates to an article having an embossed seal and a process for forming the same.

BACKGROUND OF THE INVENTION

There are many known ways to temporarily adhere thin web materials together to form a seal, including, for example, the use of adhesives, the addition of mechanical fastening elements such as Velcro, and the fusing of the webs in the melt state by heat sealing or thermal-mechanical bonding. U.S. Pat. No. 5,462,166, for example, discloses softening and fusing together thermoplastic polymeric films by the application of heat and pressure by a thermal-mechanical means. However, these methods add undesirable cost and inefficiency, as well complexity to the process for forming the seals. Additionally, seals formed in the melt state by fusing the webs together can undesirably tear at locations other than the seal and have stiff, plastic-like seals that are not appealing to users. Furthermore, these known sealing methods produce a seal that can exhibit a relatively loud noise when the two webs are separated and the seal is broken, for example, the characteristic loud sound of breaking of a Velcro seal.

Despite the knowledge in the art, there remains a desire to develop a more efficient process for making an article having a seal and for articles having a seal that is quiet when broken (i.e., when the two webs are separated at the seal). This is especially true for articles used as packaging for feminine care products. It is highly desirable to have sealed package that produces little to no noise when opening such packaging; allowing the user to more discretely open the packaging.

SUMMARY OF THE INVENTION

In one embodiment, an article includes at least two webs, and an embossed seal joining a portion of the at least two webs. The seal includes concentric discrete extended elements having open proximal ends surrounded by lands formed in the at least two webs. Portions of the discrete extended elements can have a thickness thinner than the lands. For example, distal ends and/or sidewalls of the discrete extended elements can be thinned relative to the lands. The concentric discrete extended elements of the co-formed webs are nested and can have high interfacial surface area.

In another embodiment, a process includes feeding at least two webs between a pressure source and a forming structure comprising a plurality of discrete forming elements selected from the group consisting of discrete apertures, discrete depressions, discrete protruded elements, and combinations thereof. The process further includes applying pressure from the pressure source against the webs and the forming structure sufficient to conform the at least two webs to the discrete forming elements of the forming structure, thereby forming an embossed seal comprising a plurality of concentric discrete extended elements having open proximal ends.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Disclosed herein is an article having a seal adhering portions of at least two webs and a process for forming the article that overcomes one or more of the aforementioned shortcomings of the prior art. Specifically, embodiments of the article now make possible an article that is substantially quieter upon separation of the at least two webs. Embodiments of the process now make possible a more efficient web sealing process. For example, embodiments of the article and the process can now make possible the ability to avoid the use of costly adhesives or additional mechanical adhering elements, such as hooks/loops (i.e. Velcro) and ridges/grooves, and complex processes associated with applying adhesives or the mechanical adhering elements. Embodiments of the article and process can also make possible the ability to avoid the use of complex processes that melt and fuse the two webs together to form the seal. Such seals can be very loud and/or lead to tearing of the webs (rather than separation at the seal) upon separation.

Figure 3A:
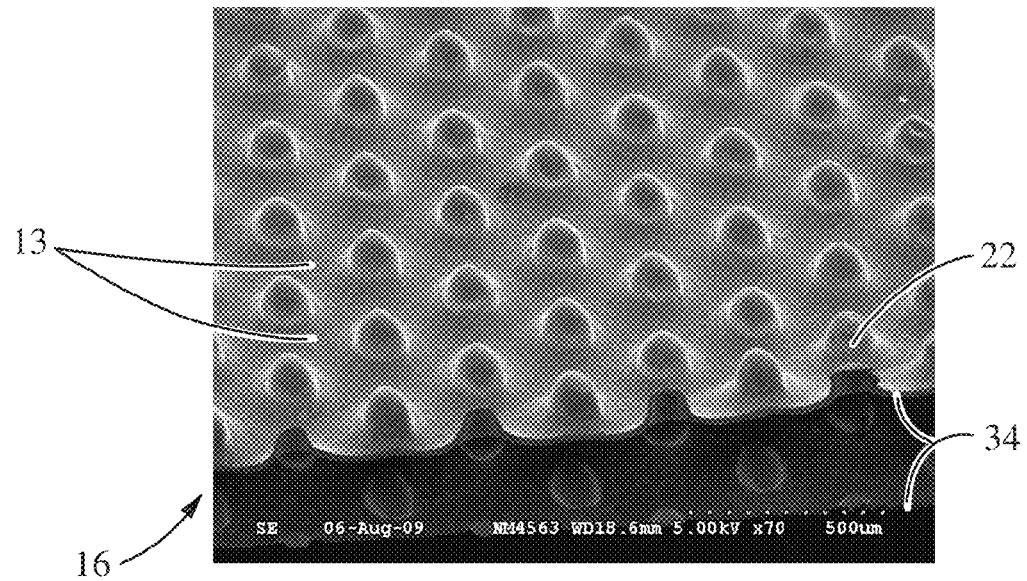
FIG. 3A is a Scanning Electron Microscopy (SEM) image of an embossed seal in accordance with an embodiment of the disclosure.
Figure 3B:
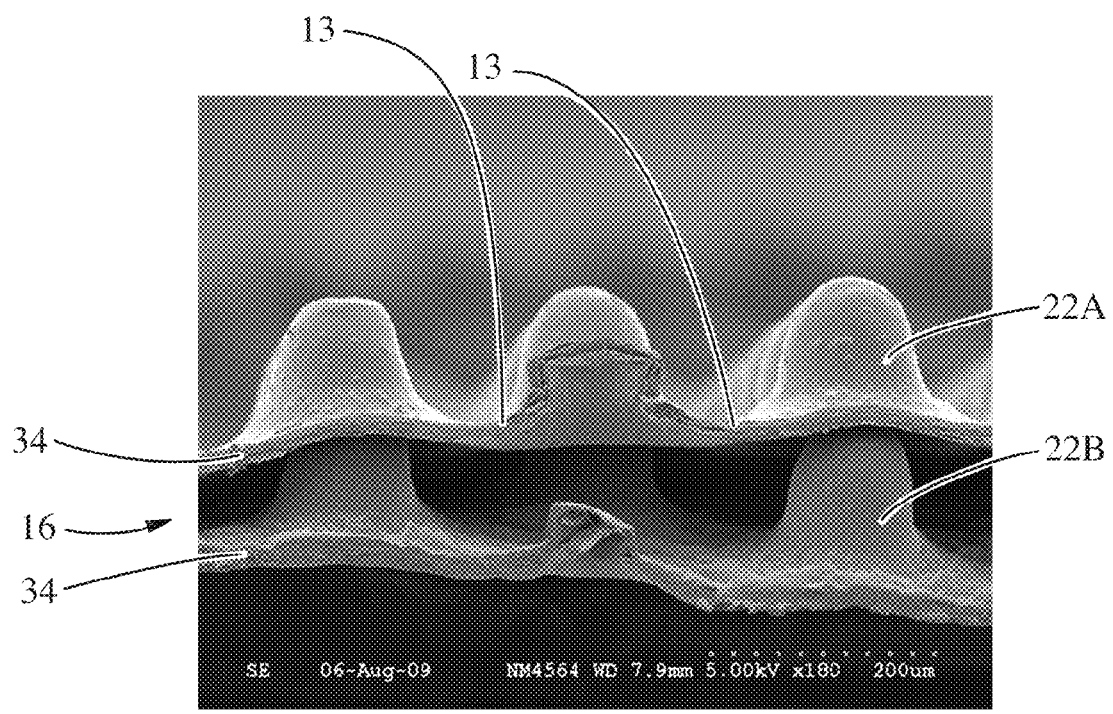
FIG. 3B is a zoomed-in SEM image of the embossed seal of FIG. 3A.

With reference to FIGS. 3A and 3B, in one embodiment, the article generally includes at least two web layers and an embossed seal 16 joining portions of the at least two web layers. The seal includes concentric discrete extended elements 22 surrounded by lands 13 formed in the at least two webs 34. The discrete extended elements 22 can be thinned relative to the lands 13. For example, distal ends and/or sidewalls of the discrete extended elements 22 can be thinned.

The concentric discrete extended elements of the co-formed webs are nested and have high interfacial surface area.

The discrete extended elements 22 extend in the z-direction to form three dimensional co-formed elements. The concentric discrete extended elements 22 are believed to generate high shear strength, preventing separation of the at least two webs during manipulation of the article. Surprisingly, even without adhesives, additional mechanical adhering elements, or melt fusing of the webs, seals can also have very high peel strengths.

Without intending to be bound by theory, it is believed that the strength of the embossed seal 16 is a function of the high interfacial surface area of the nested, co-formed regions of the at least two webs, the ability of the at least two webs 34 to adhere to themselves and to each other, and the ease with which the embossed seal 16 can be deformed. When the embossed seal 16 comprises discrete extended elements 22 having closed distal ends, it is further believed that a vacuum is created between the concentric discrete extended elements 22, which creates a suction type force holding the webs 34 together, thereby increasing the peel strength of the embossed seal 16.

The interfacial surface area of the at least two webs is a function of at least the geometry of the discrete extended elements 22 and the density of the discrete extended elements 22 in the embossed seal 16. It is believed that the peel strength of the embossed seal 16 increases with increasing interfacial surface area.

The ability of the at least two webs 34 to adhere to themselves and to each other is a function of at least the coefficient of friction the webs, the surface energies of the webs, and attractive forces such as van der Waals forces, dipole-dipole interactions, electrostatic forces, hydrogen bonds, and the like between the two webs and/or between contacting portions of the same web. It is believed that the peel strength of the embossed seal 16 generally increases with an increasing ability of the at least two webs 34 to adhere to themselves and to each other.

It is also believed that the peel strength increases if the embossed seal 16 is more flexible, rather than rigid. With a more flexible embossed seal, the at least two webs 34 can move and flex together and, thus, remain in intimate contact in the co-formed regions when being flexed. It is believed that more flexible seals result when lower modulus and or lower gauge precursor webs are used. The at least two webs 34 may have a greater tendency to separate when flexed if the embossed seal 16 is rigid, and such separation could weaken the peel strength of the embossed seal 16.

The process of forming the embossed seal 16 generally includes feeding at least two webs between a pressure source and a forming structure 10 comprising a plurality of discrete forming elements 11. The forming elements 11 can include, for example, discrete protruded elements 15, discrete apertures 12, discrete depressions 14, or combinations thereof. The process further includes, applying pressure from the pressure source against the at least two webs and the forming structure 10 sufficient to conform portions of the at least two webs to the discrete forming elements 11 thereby forming an embossed seal 16. The embossed seal 16 includes a plurality of concentric discrete extended elements 22 having open proximal ends. These aspects of the article and the process are described in further detail below.

Forming Structure

Figure 1:
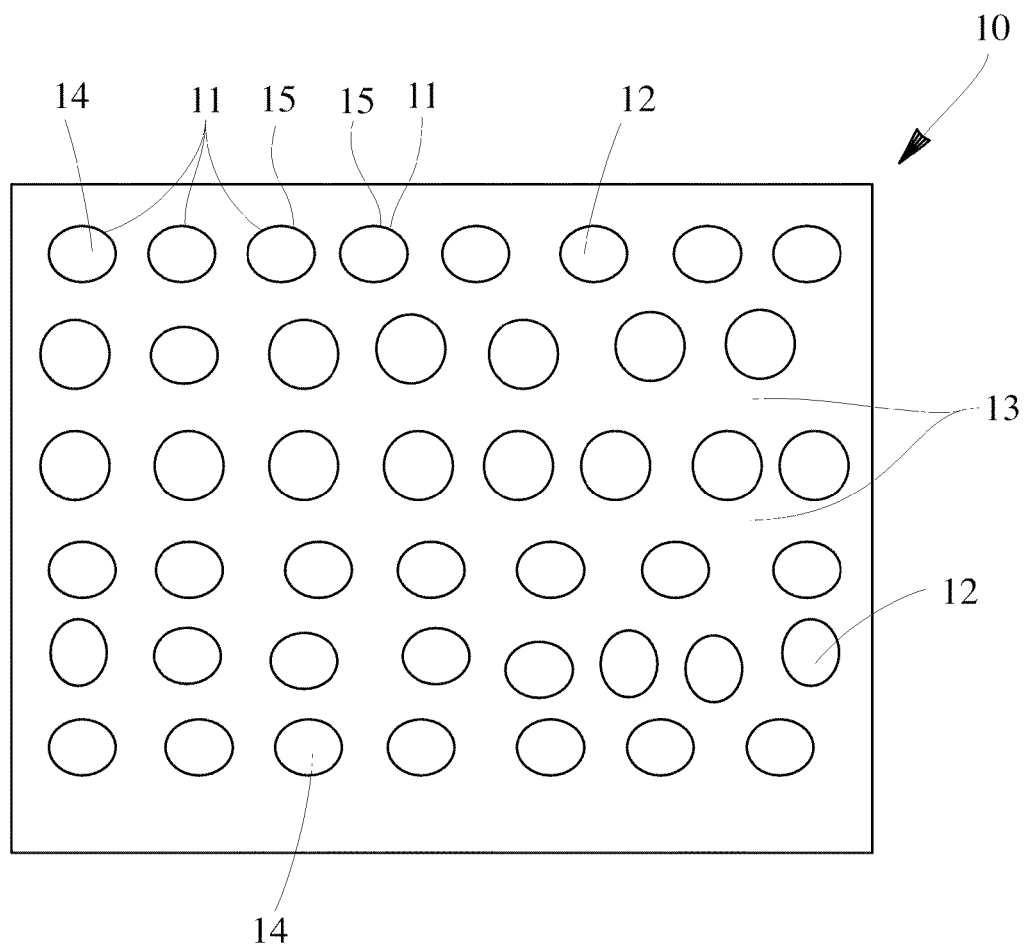
FIG. 1 is a top view of a forming structure in accordance with an embodiment of the disclosure.

Referring to FIGS. 1 and 2, a forming structure 10 useful in the process of the present disclosure includes a plurality of discrete forming elements 11. The discrete forming elements 11 can include, discrete protruded elements 15, discrete apertures, discrete depressions, or a combination thereof. The forming structure 10 can further include lands completely surrounding the discrete forming elements 11. The discrete forming elements 11 of the forming structure 10 can be small in scale relative to typical patterns used on forming structures in conventional embossing processes. The process of the disclosure can produce embossed seals that include relatively high aspect ratio extended elements 11 with thinned distal ends 24 and/or sidewalls, even without heating webs and even at high speeds.

Figure 2A:
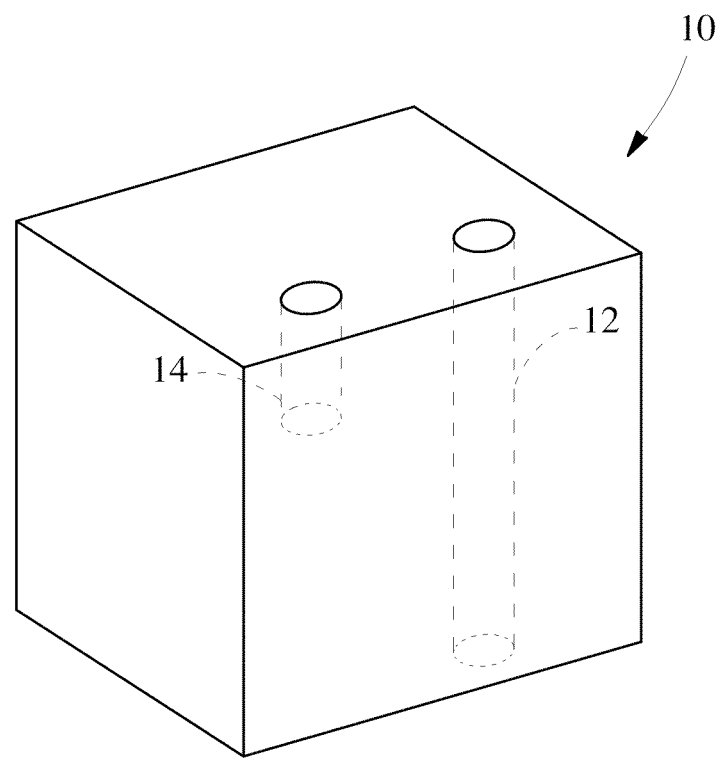
FIG. 2A is a perspective view of a forming structure in accordance with an embodiment of the disclosure illustrating the distinction between apertures and depressions.

The forming structure 10 is sometimes referred to as a forming screen. FIG. 2A illustrates the distinction between apertures 12 and depressions 14. As used herein, "apertures" refers to an opening in the forming structure 10 that does not include a bottom surface limiting the depth of the opening. In contrast, as used herein, "depressions" refers to an opening in the forming structure 10 having a bottom surface limiting the depth of the opening to be less than the thickness of the forming structure 10. The bottom surface can be, for example, porous or non-porous. For example, the bottom surface can include an opening, having a width smaller than the diameter of the depression 14, that vents the depression 14 by allowing air to pass through the depression 14. In one embodiment, the forming structure 10 has a means to allow any air trapped under the web to escape. For example, a vacuum assist can be provided to remove the air under the web so as not to increase the required compliant pressure. The bottom surface can be flat, rounded, or sharp. The forming structure 10 can be a solid roll, or have a thickness of about 25 microns to about 5000 microns, or about 100 microns to about 3000 microns. The apertures 12 and depressions 14 can have a depth of about 10 microns to about 500 microns, or about 25 microns to about 5000 microns. As used herein, the depth of the aperture corresponds to the thickness of the forming structure because the aperture 12 has no bottom surface limiting its depth. In one embodiment the apertures 12 and depressions 14 can have a depth substantially equal to the thickness of at least one of the webs, at least twice the thickness of at least one of the webs, or at least three times the thickness of at least one of the webs. Preferably, the apertures 12 and depressions 14 have a depth that is at least three times the total thickness of the webs.

The perimeter of the apertures 12 or depressions 14 on the web contacting surface of the forming structure 10 can have a straight edge or can have a radius of curvature as measured from the web contacting surface of the forming structure 10 into the aperture 12 or depression 14. The radius of curvature can be about 0 microns to about 2000 microns, preferably about 0 microns to about 25 microns, and more preferably about 2 microns to about 25 microns. In one embodiment, an angled taper, commonly known as a chamfer, is used. In one embodiment a combination of straight edges and radii are used.

Figure 2B:
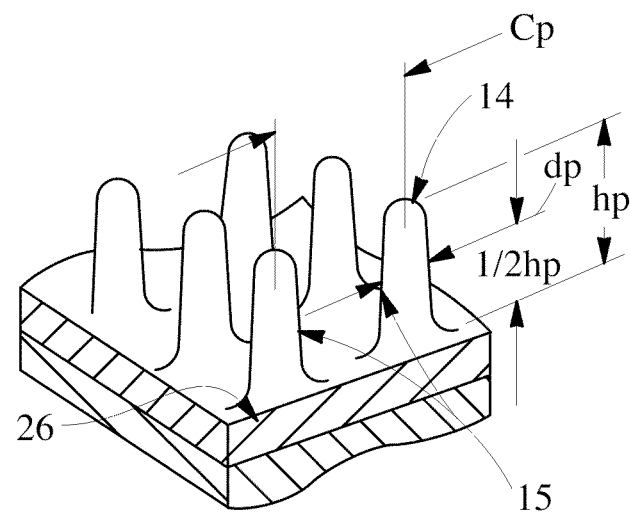
FIG. 2B is an enlarged perspective view of a portion of the forming structure having discrete protruded elements.

The discrete protruded elements 15 can have a height of at least about 50 microns, at least about 75 microns, at least about 100 microns, at least about 150 microns, at least about 250 microns, or at least about 380 microns. The discrete protruded elements 15 can have a diameter, which for a generally cylindrical structure is the outside diameter. For non-uniform cross-sections, and/or non-cylindrical structures of protruded elements 15, diameter dp is measured as the average cross-sectional dimension of protruded elements 15 at ½ the height hp of the protruded elements 15, as shown in FIG. 2B. The discrete protruded elements 15 can have diameter dp that can be from about 10 microns to about 5,000 microns, about 50 microns to about 5,000 microns, about 50 microns to about 3,000 microns, about 50 microns to about 500 microns, about 65 microns to about 300 microns, or about 75 microns to about 200 microns. In one embodiment, the discrete protruded elements 15 of the forming structure 10 will have a diameter of less than about 500 microns.

For each protruded element 15, a protruded element aspect ratio, defined as hp/dp, can be determined. Protruded elements 15 can have an aspect ratio hp/dp of at least about 0.5, at least about 0.75, at least about 1, at least about 1.5, at least about 2, at least about 2.5, or at least about 3 or higher. In general, because the actual height hp of each individual protruded element 15 may vary, an average height ("$hp_{avg}$") of a plurality of protruded elements 15 can be determined by determining a protruded element average minimum amplitude ("$Ap_{min}$") and a protruded element average maximum amplitude ("$Ap_{max}$") over a predetermined area of forming structure 10. Likewise, for varying cross-sectional dimensions, an average protrusion diameter ("$dp_{avg}$") can be determined for a plurality of protrusions 15. Such amplitude and other dimensional measurements can be made by any method known in the art, such as by computer aided scanning microscopy and related data processing. Therefore, an average aspect ratio of the protruded elements 15, ("$ARp_{avg}$") for a predetermined portion of the forming structure 10 can be expressed as $hp_{avg}/dp_{avg}$.

The discrete protruded elements 15 of the forming structure 10 can have distal ends 24 that are flat, rounded or sharp, depending upon whether it is desired to produce an embossed seal 16 having discrete extended elements 22 with distal ends 24 that are open (requiring a sharper protruded element on the forming structure 10) or closed (requiring a more rounded protruded element on the forming structure 10). The rounded distal ends 24 of the discrete protruded elements 15 of the forming structure 10 can have a certain tip radius, such as from about 5 microns to about 150 microns, from about 10 microns to about 100 microns, from about 20 to about 75 microns, or from about 30 microns to about 60 microns.

The sidewalls of the discrete protruded elements 15 can be completely vertical or can be tapered. In one embodiment, the discrete protruded elements 15 have tapered sidewalls, as tapered sidewalls can have an impact on durability and longevity of the pressure source. For example, when a compliant substrate 44 the tapered sidewalls can ease the compression or tension on compliant substrate 44 as it conforms around discrete forming elements 11 of the forming structure 10. This can also allow the web to more easily separate from the forming structure 10 after embossing. In one embodiment, the sidewalls will typically have a degree of taper of from about 0° to about 50°, from about 2° to about 30°, or from about 5° to about 25°.

In one embodiment, the forming elements can have varying geometries, such as height of the protruded elements 15 and depth of the apertures 12 or depressions 14, which can selectively impact the bond strength of certain regions of the web material. For example, the forming elements can gradually increase in height or over a range of tens or hundreds of adjacent protruded elements, which can result in the web having discrete extended elements 22 with varying heights, which in turn can result in an embossed seal 16 having a strength gradient. Other features of the forming structure which results in corresponding features of the discrete extended elements 22 can be adjusted to form an embossed seal 16 having a strength gradient. For example, the forming structure can include an area density gradient of forming elements.

In one embodiment, the protruded elements can be spherical, ellipsoid, or snowman-shaped, having different or varying diameters along then height of the protruded element.

The apertures 12 or depressions 14 have a diameter, which for a generally cylindrical structure is the inside diameter. For non-uniform cross-sections, and/or non-cylindrical structures of apertures 12 or depressions 14, diameter is measured as the average cross-sectional dimension of apertures 12 or depressions 14 at the top surface of the forming structure 10. Each aperture 12 or depression 14 can have diameter of about 40 microns to about 2,000 microns. Other suitable diameters include, for example, about 50 microns to about 500 microns, about 65 microns to about 300 microns, about 75 microns to about 200 microns, about 10 microns to about 5000 microns, about 50 microns to about 5000 microns, about 500 microns to about 5000 microns, or about 800 microns to about 2,500 microns.

In one embodiment, the diameter of apertures 12 or depressions 14 is constant or decreases with increasing depth. In another embodiment, the diameter of the apertures 12 or depressions 14 increases with increasing depth. For example, the discrete apertures 12 or depressions 14 can have a first diameter at a first depth and a second diameter at a second depth deeper than the first depth. For example, the first diameter can be larger than the second diameter. For example, the second diameter can be larger than the first diameter.

The sidewalls of the discrete apertures 12 or depressions 14 can be completely vertical or can be tapered. In one embodiment, the discrete apertures 12 or depressions 14 have tapered sidewalls. This can allow the webs 34 to more easily separate from the forming structure 10 after embossing. In one embodiment, the sidewalls will typically have a degree of taper of about 0° to about −50° to about 50°, about −30° to about 30°, about 0° to about 50°, about 2° to about 30°, or about 5° to about 25°.

The discrete forming elements 11 of the forming structure 10 can have a variety of different cross-sectional shapes, such as generally columnar or non-columnar shapes, including circular, oval, hour-glass shaped, star shaped, polygonal, and the like, and combinations thereof. Polygonal cross-sectional shapes include, but are not limited to, rectangular, triangular, hexagonal, or trapezoidal. In one embodiment, the discrete depressions can have a length substantially equal to the length of the forming structure 10 so as to form grooves about substantially the entire length of the forming structure 10. In another embodiment, the discrete protruded elements 15 can have a length substantially equal to the length of the forming structure 10 so as to form an extended protruded element about substantially the entire length of the forming structure 10. For example, when the forming structure 10 is in the form of a roll, the grooves and/or extended protruded elements can be formed about the entire circumference of the roll. The grooves and/or extended protruded elements can be substantially straight (e.g., consistently parallel to the edge of the roll) or can be wavy.

In general, the forming structure 10, for a given portion of thereof, will include at least about 4 discrete forming elements 11 per square centimeter, at least about 10 discrete forming elements 11 per square centimeter, at least about 95 discrete forming elements 11 per square centimeter, at least about 240 discrete forming elements 11 per square centimeter, about 350 to about 10,000 discrete forming elements 11 per square centimeter, about 500 to about 5,000 discrete forming elements 11 per square centimeter, or about 700 to about 3,000 discrete forming elements 11 per square centimeter.

The discrete forming elements 11 can have an average edge-to-edge spacing between two adjacent apertures 12 or depressions 14 of about 30 microns to about 1000 microns, about 30 microns to about 800 microns, about 150 microns to about 600 microns, or about 180 microns to about 500 microns.

In certain embodiments, a portion (or area) of the forming structure 10 can include area densities of discrete forming elements 11 as described in the preceding paragraph, while other portions (or areas) of the forming structure 10 may include no discrete forming elements 11. The areas of the forming structure 10 having no discrete forming elements 11 can be located in a different horizontal plane. In other embodiments, the discrete forming elements 11 of the forming structure 10 can be located in different horizontal planes of the forming structure 10. The regions having no discrete forming elements 11 and/or the regions having discrete forming elements 11 located in different horizontal planes of the forming structure 10 can be in the form of a specific pattern or design, such as a flower, bird, ribbon, wave, cartoon character, logo, and the like, so that the embossed seal 16 will have a region that stands out visually from, and/or has a different hand feel when touched relative to, the remainder of the web. For example, the embossed seal 16 can include a non-embossed region that stands out visually from, and/or has a different hand feel from embossed regions. U.S. Pat. No. 5,158,819 provides suitable examples of forming structures for use in these embodiments.

In one embodiment, a ratio of the average depth of the apertures 12 or depressions 14 or the average height of the discrete protruded elements 15 to the thickness of at least one of the webs 34 is at least about 1:1, at least about 2:1, at least about 3:1, at least about 4:1, at least about 5:1, or at least about 10:1. This ratio can be important to ensure the webs 34 are sufficiently stretched so that each becomes permanently deformed to create an embossed seal 16, especially at desirable process conditions and speed.

Forming structure 10 can be made of any material or materials that can be formed to have discrete forming elements 11 having the necessary dimensions to make an embossed seal 16 and is dimensionally stable over process temperature and pressure ranges experienced by forming structure 10.

In one embodiment, discrete forming elements 11 are made integrally with forming structure 10. That is, the forming structure 10 is made as an integrated structure, either by removing material or by building up material. For example, the forming structure 10 having the required relatively small scale discrete forming elements 11 can be made by local, selective removal of material, such as by chemical etching, mechanical etching, or by ablating by use of high-energy sources such as electrical-discharge machines (EDM) or lasers, or by electron beam (e-beam), or by electrochemical machining (ECM). In one embodiment, the forming structure 10 may be constructed by a photo etched laminate process generally in accordance with the teachings of U.S. Pat. No. 4,342,314.

In one method of making a suitable forming structure 10, a base material susceptible to laser modification is laser "etched" to selectively remove material to form apertures 12 or depressions 14. By "susceptible to laser modification", it is meant that the material can be selectively removed by laser light in a controlled manner, recognizing that the wavelength of light used in the laser process, as well as the power level, may need to be matched to the material (or vice-versa) for optimum results. Laser etching can be achieved by known laser techniques, selecting wavelength, power, and time parameters as necessary to produce the desired protruded element dimensions. Currently known materials susceptible to laser modification include thermoplastics such as polypropylene, acetal resins such as DELRIN® from DuPont, Wilmington Del., USA, thermosets such as crosslinked polyesters, or epoxies, or even metals such as aluminum, copper, brass, nickel, stainless steel, or alloys thereof. Optionally, thermoplastic and thermoset materials can be filled with particulate or fiber fillers to increase compatibility with lasers of certain wavelengths of light and/or to improve modulus or toughness to make more durable apertures 12 or depressions 14. For example, certain polymers, such as PEEK, can be laser machined to higher resolution and at higher speeds by uniformly filling the polymer with sufficient amounts of hollow carbon nanotube fibers.

In one embodiment, a forming structure 10 can be laser machined in a continuous process. For example, a polymeric material such as DELRIN® can be provided in a cylindrical form as a base material having a central longitudinal axis, an outer surface, and an inner surface, the outer surface and inner surface defining a thickness of the base material. It can also be provided as a solid roll. A moveable laser source can be directed generally orthogonal to the outer surface. The moveable laser source can be moveable in a direction parallel to the central longitudinal axis of the base material. The cylindrical base material can be rotated about the central longitudinal axis while the laser source machines, or etches, the outer surface of the base material to remove selected portions of the base material in a pattern that defines a plurality of discrete apertures 12 or depressions 14 and/or discrete protruded elements 15.

The forming structure 10 can be in the form of a flat plate, a roll, a belt, an endless belt, a sleeve, or the like. In one preferred embodiment, the forming structure 10 is in the form of a roll. In another preferred embodiment, the forming structure 10 is in the form of an endless belt. Endless belts can be formed in accordance with the teachings of U.S. Pat. Nos. 7,655,176, 6,010,598, 5,334,289, and 4,529,480.

The forming structure can be utilized in a low strain rate process, such as that described in U.S. Application No. 2008/0224351 A1, to produce an embossed web of the present invention wherein the activation belt is a solid or compliant substrate.

If the forming structure 10 includes protruded elements 15 and discrete apertures 12 and depressions 14, the discrete extended elements 22 can be formed in the webs 34 extending from the surface of the webs 34 opposite the surface from which the discrete extended elements 22 formed by the apertures 12 or depressions 14 of the forming structure 10 are formed. As a result, a two-sided embossed seal 16 can be created, having different patterns or dimensions of extended elements 22 on each side of the embossed seal 16. Depending upon the pressure generated between the forming structure 10 and compliant substrate 44, as well as the geometric shapes of the apertures 12 or depressions 14 and optional pillars or ridges of the forming structure 10, the discrete extended elements 22 of the embossed seal 16 can have closed or open distal ends 24.

Pressure Source

The pressure source utilized to provide a force against the forming structure 10 can be, for example, a compliant substrate 44, a static pressure plenum, a velocity pressure source, or combinations thereof. One example of a device suitable for providing velocity air pressure to conform the precursor web to the forming structure is a high pressure air knife. High pressure air knives are commercially available from, for example, Canadian Air Systems. Another example of a suitable device and process utilizing air pressure to conform the precursor web to the forming structure is described in U.S. Pat. No. 5,972,280. An example of a device suitable for providing water pressure to conform the precursor web to the forming structure is a water plenum, such as that described in U.S. Pat. No. 7,364,687.

For example, a suitable process for making the embossed seal 16 is a hydroforming process. Non-limiting examples of hydroforming processes are described in U.S. Pat. No. 4,609,518 and U.S. Pat. No. 4,846,821. A forming structure and web as described herein can be utilized in such hydroforming processes.

Another suitable process, for example, for making the embossed seal 16 is a vacuum forming process. Non-limiting examples of vacuum forming processes are described in U.S. Pat. Nos. 4,456,570 and 4,151,240, and U.S. Application Publication No. 2004/0119207 A1. A forming structure and precursor web as described herein can be utilized in such vacuum forming processes to produce the embossed seal 16 of the present disclosure. Other suitable processes are described in U.S. Pat. No. 4,846,821 and U.S. Application Publication No. 2004/0119207 A1.

Compliant Substrate

Figure 7:
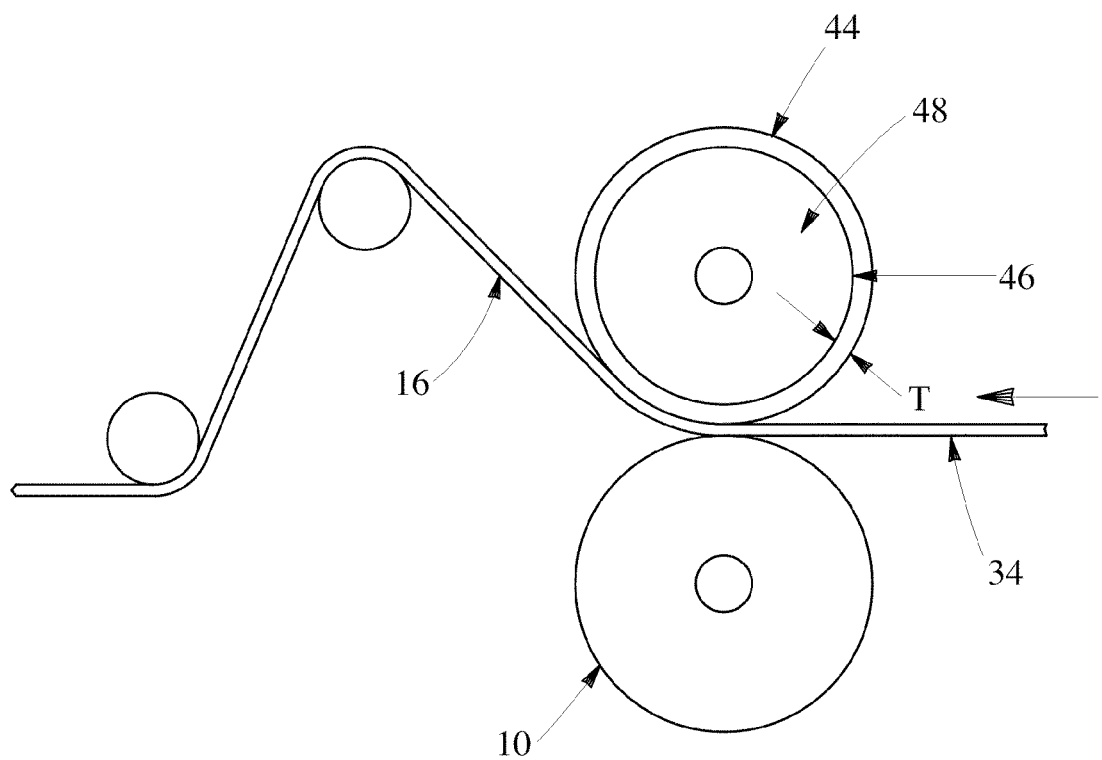
FIG. 7 is a schematic illustration of a continuous process for making an embossed web in accordance with an embodiment of the disclosure; and, FIG. 8 is a high magnification optical microscopy image of the side view of a forming structure having discrete extended elements for use in a process in accordance with an embodiment of the disclosure.

Referring to FIG. 7, at a minimum, the outer surface of the compliant substrate 44 (i.e., the surface of the compliant substrate 44 oriented towards the forming structure 10) includes a compliant material 46. For example, the compliant substrate 44 can include a rigid material 48 covered by a compliant material 46. The rigid material 48 can be a metal (such as steel), a plastic, or any other material that is significantly harder than the compliant material 46. The thickness of the compliant material 46 covering the rigid material 48 will typically be no greater than about 26 mm, and preferably about 1 mm to about 26 mm, more preferably about 1 mm to about 7 mm. Alternatively, the entire compliant substrate 36 can be made of a compliant material 46.

The compliant substrate 44 or compliant material 46 can include elastomers, felts, liquid-filled bladders, gas-filled bladders, and combinations thereof. In one embodiment, the compliant substrate 44 is a porous elastomer. The compliant substrate 44, or the compliant material 46 utilized in the compliant substrate 44, preferably has resilient properties (such as compression recovery) such that the compliant material 46 rebounds fast enough to facilitate the process, especially a continuous process.

The compliant substrate 44, or the compliant material 46 utilized in the compliant substrate 44, preferably also has enough durability to emboss large quantities of web 34 material. As a result, the compliant substrate 44 preferably has a suitable degree of toughness and abrasion resistance, wherein the compliant substrate 44 will tend to be abraded by the forming structure 10 during the process.

The compliant substrate 44 can be in the form of a flat plate, a roll, a belt, an endless belt, a sleeve, or the like. In one embodiment, the compliant substrate 44 is a metal roll covered with a compliant material 46, such as an elastomer. In another embodiment, the compliant substrate 44 and the forming structure 10 are both in the form of rolls. In another embodiment, the compliant substrate 44 is a roll that has a diameter greater than the diameter of the forming structure 10 roll. In another embodiment, the compliant substrate 44 is a roll that has a diameter less than the diameter of the forming structure 10 roll. In another embodiment, the compliant substrate 44 roll has a diameter that is the same as the diameter of the forming structure 10 roll.

The compliant substrate 44, or the compliant material 46 utilized in the compliant substrate 44, will typically have a hardness of about 30 to about 90 durometer, preferably about 35 to about 80 durometer, and more preferably about 40 to about 70 durometer, on the Shore A scale. Hardness on the Shore A scale is typically determined by using an ASTM D2240 durometer, such as the Model 306 Type A Classic Style Durometer available from PTC Instruments of Los Angeles, Calif. It should be recognized that the compliant substrate 44 can exhibit varying hardness, for example lower hardness near the outer surface and higher hardness towards the inner surface of the compliant substrate 44 (i.e. varying hardness in the z-direction of the compliant substrate 44) or varying hardness across the outer surface of the compliant substrate 44 (i.e. varying hardness in the x-y plane of the compliant substrate 44).

The compliant material 46 utilized in the compliant substrate 44 will typically have a tensile modulus of about 1 to about 20 MPa, preferably about 2 to about 18 MPa, and more preferably about 3 to about 10 MPa. The tensile modulus of the compliant material 46 can be determined at a strain rate of 0.1 sec$^{-1}$.

Non-limiting examples of suitable compliant materials include natural rubber, urethane rubber, polyurethane rubber, chlorosulfonated polyethylene rubber (available under the tradename HYPALON® from DuPont), chloroprene rubber, norbornene rubber, nitrile rubber, hydrogenated nitrile rubber, styrene rubber, styrene-butadiene rubber, butadiene rubber, silicone rubber, ethylene-propylene-diene ("EPDM") rubber, isobutylene-isoprene rubber, felt (such as pressed wool felt), and the like. Particularly useful compliant materials are isoprene, EPDM, neoprene, and HYPALON® having a Shore A hardness of about 40 to about 70 durometer.

The compliant material 46 can also be a material, such as an absorbent core, that can be fed between a rigid material 48 and the forming structure 10 along with the webs 34. Such a material can serve to generate pressure against the webs 34 and forming structure 10 so as to emboss the webs 34. Such a material can then be later incorporated, along with the embossed seal 16, into a finished consumer product, such as a feminine hygiene product.

The compliant substrate 44 can optionally include recessed regions of a depth sufficient to prevent the embossing of the webs 34 in the particular region, or only minimally emboss the webs 34 in the particular region.

Static Pressure Plenum

Figure 6:
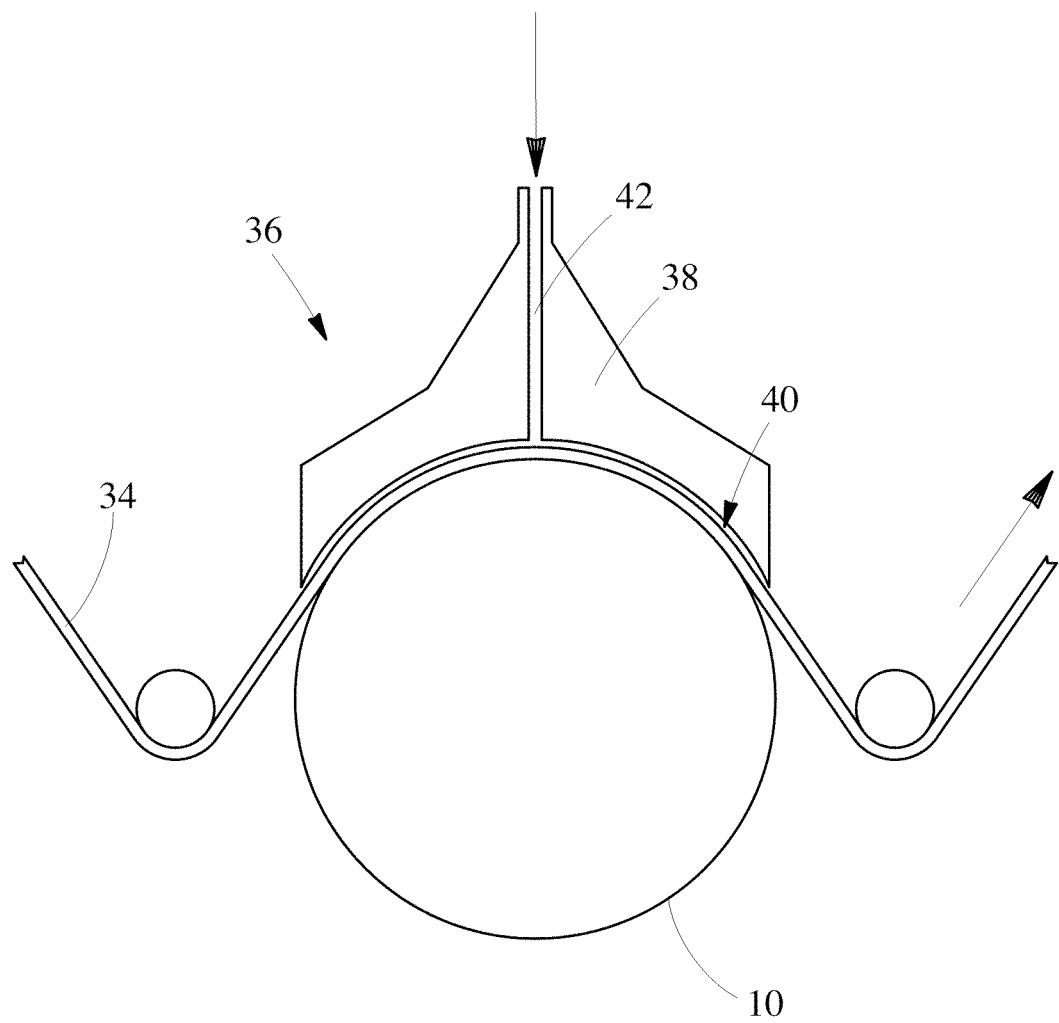
FIG. 6 is a schematic representation of a process in accordance with an embodiment of the disclosure, illustrating a static gas pressure plenum.

Referring to FIG. 6, a static pressure plenum 36 is utilized to provide a force against the webs 34 to conform the webs 34 to the discrete forming elements 11 of the forming structure 10. Preferably, the static pressure plenum 36 is a static gas pressure plenum. The gas can be air, nitrogen, carbon dioxide, and combinations thereof.

The static pressure plenum 36 exerts a pressure on the webs 34. The static gas pressure plenum 36 can include a hood 38 which defines a plenum 40 adjacent the webs 34. The hood 38 can include at least one high pressure gas inlet 42 allowing high pressure gas or other fluid to enter the hood 38 creating the static pressure conditions. Under static gas pressure conditions, there is no velocity and density impinging upon the unembossed webs 34 as with a velocity pressure source such as an air knife. Rather, a static high gas pressure is maintained in the hood 38 which creates a pressure differential across the webs, between the static pressure plenum 36 facing surface of the webs 34 and the forming structure 10 facing surface of the webs 34. The pressure differential is sufficient to conform the webs 34 to the discrete forming elements 11 of the forming structure 10. The pressure differential can be enhanced, for example, by applying a vacuum on the forming structure 10 facing surface of the webs 34.

Web

At least two webs or web layers are joined by an embossed seal 16. The at least two webs can be, for example, different, overlapping portions of the same web. For example, a web material can be folded, for example, in a tri-fold configuration, and overlapping portions of the web material can be joined by an embossed seal 16. Alternatively, the at least two webs can be different webs. Suitable webs include materials that can be deformed by the pressure source, such that the webs conform to the discrete elements 11 of the forming structure 10 to produce an embossed seal 16 joining the two webs. Preferably, the webs have the ability to adhere to themselves and/or other web materials.

The webs typically include synthetic material, metallic material, biological material (in particular, animal-derived materials), or combinations thereof. The at least two webs can be the same material or can be different materials. The webs can optionally include cellulosic material. In one embodiment, the webs are free of cellulosic material. Non-limiting examples of suitable webs include films, such as polymeric or thermoplastic films, foils, such as metallic foils (e.g. aluminum, brass, copper, and the like), webs comprising sustainable polymers, foams, fibrous nonwoven webs comprising synthetic fibers (e.g. TYVEK®), collagen films, chitosan films, rayon, cellophane, and the like. Suitable webs further include laminates or blends of these materials.

If the webs are fibrous webs, the fibrous webs typically will have a high density such that it behaves similar to a film material. One example of such a high density fibrous web is TYVEK®.

In one embodiment, the webs are polymeric films. Suitable polymeric films include thermoplastic films such as polyethylene, polypropylene, polystyrene, polyethylene terephthalate (PET), polymethylmethacrylate (PMMA), polyvinyl alcohol (PVA), nylon, polytetrafluoroethylene (PTFE) (e.g., TEFLON), or combinations thereof. Suitable polymeric films can include blends or mixtures of polymers.

In certain embodiments, the webs can comprise a sustainable polymer, such as polylactides, polyglycolides, polyhydroxyalkanoates, polysaccharides, polycaprolactones, and the like, or mixtures thereof.

The thickness of each of the webs prior to embossing will typically range from about 5 to about 300 microns, about 5 microns to about 150 microns, about 5 microns to about 100 microns, or about 15 microns to about 50 microns. Other suitable thicknesses includes about 1, 2, 3, 4, 5, 6, 7, 8, 9, 10, 20, 30, 40, 50, 60, 70, 80, 90, 100, 150, 200, 250, or 300 microns.

Webs, such as polymeric webs, will typically have a glass transition temperature of about −100° C. to about 120° C., or about −80° C. to about 100° C., or other suitable ranges. Webs, such as polymeric webs, can have a melting point of about 100° C. to about 350° C. For example, a web formed of LDPE or a blend of LDPE and LLDPE has a melting pointing of about 110° C. to about 122°. A web formed of polypropylene has a melting point of about 165° C. A web formed of polyester has a melting point of about 255° C. A web formed of Nylon 6 has a melting point of about 215° C. A web 34 formed of PTFE has a melting point of about 327° C.

In one embodiment, the process is carried out at a temperature less than the melting point of the webs. For example, the process can be carried out at 10° C. less than the melting point of the webs. In another embodiment, the process is carried out at a temperature substantially equal to the melting point of the webs. In one embodiment, the process is carried out at a temperature greater than the glass transition temperature of the webs. Regardless of the temperature used in the process, the process conditions on the whole are selected so as to not melt-fuse the webs. For example, higher temperatures may be coupled with short dwell times such that none of the at least two web materials melt to cause fusion of the webs.

Optionally, the webs 34 may be plasticized to decrease the elastic moduli and/or make them less brittle prior to embossing in the process.

In one embodiment, the webs 34 are strain hardening. The strain hardening properties of the webs can be desirable to facilitate conformation of the webs to the discrete forming elements 11 of the forming structure 10. This can be preferred for producing embossed seals wherein closed distal ends 24 of the extended elements 22 of the embossed seal 16 are desired.

The webs 34 can be any material, such as a polymeric film, having sufficient material properties to be formed into an embossed seal 16 described herein by the embossing process of the disclosure. At least one of the at least two webs 34 will typically have a yield point and the webs 34 are preferably stretched beyond its yield point to form an embossed seal 16. That is, the webs 34 should have sufficient yield properties such that the webs 34 can be strained without rupture to an extent to produce the desired discrete extended elements 22 with closed distal ends 24 or, in the case of an embossed seal comprising discrete extended elements 22 having open distal ends 24, rupture to form open distal ends 24. As disclosed below, process conditions such as temperature can be varied for a given polymer to permit it to stretch with or without rupture to form the embossed seal 16 having the desired discrete extended elements 22. In general, therefore, it has been found that preferred starting materials to be used as the webs 34 exhibit low yield and high-elongation characteristics. In addition, as discussed previously, the webs preferably strain harden. Examples of films suitable for use as the webs 34 include films comprising low density polyethylene (LDPE), linear low-density polyethylene (LLDPE), polypropylene, and blends thereof.

The webs 34 should also be sufficiently deformable and have sufficient ductility for use as webs 34. The term "deformable" as used herein describes a material which, when stretched beyond its elastic limit, will substantially retain its newly formed conformation, as well as exhibit thinning at or near the distal ends 24 of the discrete extended elements 22 of the resulting embossed seal 16.

One material found suitable for use as the webs 34 is DOWLEX 2045A polyethylene resin, available from The Dow Chemical Company, Midland, Mich., USA. A film of this material having a thickness of 20 microns can have a tensile yield of at least 12 MPa; an ultimate tensile of at least 53 MPa; an ultimate elongation of at least 635%; and a tensile modulus (2% Secant) of at least 210 MPa (each of the above measures determined according to ASTM D 882). Other suitable webs include polyethylene film that is about 25 microns (1.0 mil) thick and has a basis weight of about 24 grams per square meter ("gsm") available from available from RKW US, Inc. (Rome, Ga.) and polyethylene/polypropylene film having a basis weight of about 14 gsm and a thickness of about 15 microns available from RKW US, Inc.

The webs 34 can each be a laminate of two or more web layers, and can be a co-extruded laminate. For example, each web can include two layers, and each web can include three layers, wherein the innermost layer is referred to as a core layer, and the two outermost layers are referred to as skin layers. In one embodiment, at least one of the webs includes a three layer coextruded laminate having an overall thickness of about 25 microns (0.001 in.), with the core layer having a thickness of about 18 microns (0.0007 in.); and each skin layer having a thickness of about 3.5 microns (0.00015 in.). In one embodiment, the layers can include polymers having different stress-strain and/or elastic properties.

The webs 34 can be made using conventional procedures for producing multilayer films on conventional coextruded film-making equipment. Where layers comprising blends are required, pellets of the above described components can be first dry blended and then melt mixed in the extruder feeding that layer. Alternatively, if insufficient mixing occurs in the extruder, the pellets can be first dry blended and then melt mixed in a pre-compounding extruder followed by repelletization prior to film extrusion. Suitable methods for making the webs 34 are disclosed in U.S. Pat. No. 5,520,875 and U.S. Pat. No. 6,228,462.

In general, the ability to form high area density (or low average center-to-center spacing) discrete extended elements 22 on the embossed seal 16 can be limited by the thickness of webs 34.

In certain embodiments, the webs 34 can optionally further include a surfactant. If utilized, preferred surfactants include those from non-ionic families such as: alcohol ethoxylates, alkylphenol ethoxylates, carboxylic acid esters, glycerol esters, polyoxyethylene esters of fatty acids, polyoxyethylene esters of aliphatic carboxylic acids related to abietic acid, anhydrosorbitol esters, ethoxylated anhydrosorbitol esters, ethoxylated natural fats, oils, and waxes, glycol esters of fatty acids, carboxylic amides, diethanolamine condensates, and polyalkyleneoxide block copolymers. Molecular weights of surfactants selected can range from about 200 grams per mole to about 10,000 grams per mole. Preferred surfactants have a molecular weight of about 300 to about 1,000 grams per mole.

If utilized, the surfactant level initially blended into the webs can be as much as 10 percent by weight of the total web. Surfactants in the preferred molecular weight range (300-1, 000 grams/mole) can be added at lower levels, generally at or below about 5 weight percent of the total web.

In various embodiments, the webs can also include additives to enhance a web's ability to adhere to itself and other webs. Any known additives for increasing a webs adhesive ability can be used. For example, low molecular weight polymers, for example, polyisobutene (PIB) and poly(ethylenevinylacetate) (EVA) copolymer can be added to the web materials. When used with LDPE, for example, PIB and EVA have chains readily interact with each other and their lower molecular weight makes them more mobile within the host polymer matrix.

Preferably, the webs are free of release agents and/or low surface energy chemical functional groups on the surface of the webs. It has been found that the presence of low surface energy chemical functional groups on the surface of the webs can reduce the bond strength of the webs. For example, silicone adhesive release agents topically applied to one or more of the web surfaces to be bonded can render a resulting bond weak, especially as compared to a bond formed in the same web material without the topically applied silicone adhesive release agent. It is believed that the attractive forces between the web surfaces are reduced by low surface energy treatments. Other low surface energy surface treatments include fluorocarbons.

In certain embodiments, the webs can also include titanium dioxide in the polymer blend. Titanium dioxide can provide for greater opacity of the embossed seal 16. Titanium dioxide can be added at up to about 10 percent by weight of the web, such as low density polyethylene.

Other additives, such as particulate material, e.g., carbon black, iron oxide, mica, calcium carbonate ($CaCO_3$), particulate skin treatments or protectants, or odor-absorbing actives, e.g., zeolites, can optionally be added in one or more layers of the webs 34. In some embodiments, embossed seals comprising particulate matter, when used in skin-contacting applications, can permit actives to contact the skin in a very direct and efficient manner. Specifically, in some embodiments, formation of discrete extended elements 22 can expose particulate matter at or near the distal ends 24 thereof. Therefore, actives such as skin care agents can be localized at or near distal ends 24 of the discrete extended elements 22 to permit direct skin contact with such skin care agents when the embossed seal 16 is used in skin contacting applications.

The average particle size of the particulate material, if utilized in the webs 34, will typically be 0.1 microns to about 200 microns, 0.2 microns to about 200 microns, or about 5 microns to about 100 microns. The use of certain particulate materials, such as mica interference particles, can dramatically improve the visual appearance of the embossed seal 16.

The webs can also optionally include colorants, such as pigment, lake, toner, dye, ink or other agent used to impart a color to a material, to improve the visual appearance of the embossed seal 16.

Suitable pigments herein include inorganic pigments, pearlescent pigments, interference pigments, and the like. Non-limiting examples of suitable pigments include talc, mica, magnesium carbonate, calcium carbonate, magnesium silicate, aluminum magnesium silicate, silica, titanium dioxide, zinc oxide, red iron oxide, yellow iron oxide, black iron oxide, carbon black, ultramarine, polyethylene powder, methacrylate powder, polystyrene powder, silk powder, crystalline cellulose, starch, titanated mica, iron oxide titanated mica, bismuth oxychloride, and the like.

Suitable colored webs are described in co-pending U.S. application Ser. No. 12/721,947, filed Mar. 11, 2010 entitled "COLORED WEB MATERIAL COMPRISING A PLURALITY OF DISCRETE EXTENDED ELEMENTS" (P&G Case 11634) and U.S. application Ser. No. 12/721,965, filed Mar. 11, 2010 entitled "WEB MATERIAL EXHIBITING VIEWING-ANGLE DEPENDENT COLOR AND COMPRISING A PLURALITY OF DISCRETE EXTENDED ELEMENTS" (P&G Case 11635).

The webs can also optionally include fillers, plasticizers, and the like.

Embossed Web

The article having the embossed seal 16 can have various desired structural features and properties such as desired soft hand feel and an aesthetically pleasing visual appearance. The embossed seal 16 includes concentric discrete extended elements 22. As used herein, the term "concentric" refers to extended elements 22 having substantially the same center. For example, the centers of the extended elements can be offset by less than about 1000 microns, less than about 500 microns, less than about 100 microns, less than about 50 microns, or less than about 20 microns. In one embodiment, a portion of the discrete extended elements 22 are thinned relative to the lands 13 surrounding the discrete extended elements 22. For example, the distal ends and/or the sidewalls of the discrete extended elements 22 can be thinned relative to the lands 13. The concentric discrete extended elements 22 have high interfacial surface area of the nested, co-formed regions of the at least two webs. In addition, as disclosed above, it is believed that there is sufficient friction and/or attractive forces to retain the at least two webs joined at the embossed seal 16. For discrete extended elements 22 having closed distal ends 24, further suction type forces may aid in retaining the at least two films joined at the embossed seal 16. Separation of the two webs at the embossed seal 16 requires sufficient force to separate the concentric discrete extended elements 22. Such separation generates little to no noise as compared to prior art bonding methods, such as those involving fusing of the webs by heat and pressure. When the at least two layers of the article are separated at the embossed seal 16, the noise generated by the separation is noticeably less than the noise generated by a conventional seal formed by a thermo-mechanical bonding process, such as described in U.S. Pat. No. 5,462,166. For example, when the at least two layers of the article are separated at the embossed seal 16, the sound pressure level generated from the separation can be less than about 70 dB, less than about 65 dB, or less than about 60 dB, as measured by the Sound Pressure Level Test. The embossed seal 16 is substantially quieter upon separation than a seal formed by a conventional thermo-mechanical bonding process using conventional processing conditions, such as, for example, those described in U.S. Pat. No. 5,462, 166. For example, the embossed seal 16 can generate a sound pressure level upon separation that is at least about 2 dB less, at least about 3 dB, at least about 4 dB less, at least about 5 dB, at least about 6 dB less, at least about 7 dB, at least about 8 dB less, at least about 9 dB, or at least about 10 dB less than the sound pressure level generated from a seal formed by conventional thermo-mechanical bonding process having substantially the same peel strength as the embossed seal 16 and separated under the same conditions as the embossed seal 16. Substantially the same peel strength refers to a peel strength within at least about 50%, at least about 60%, at least about 70%, or at least about 80% of the peel strength of the embossed seal 16.

The embossed seal 16 can have a peel strength at least substantially equal to a conventional seal, such as a conventional thermo-mechanical seal, as measured by the Peel Strength Test. For example, the embossed seal 16 can have a peel strength that is at least within 30%, 40%, 50%, 60%, 70%, 80%, 90%, or 100% of the peel strength of a conventional, thermo-mechanical seal.

The Peel Strength Test can be performed according to the method disclosed in U.S. Pat. No. 5,462,166.

The Sound Pressure Level Test can be performed with a QUEST Technologies model 2900 Sound Meter to measure and record the sound pressure level while peeling apart the bonded web of known width and length. The microphone of the Meter is placed 5 cm from the bond to be peeled apart. The Sound Meter is operated using the A weighting factor to more closely approximate the way the human ear hears. (Standard IEC 651—Sound Level Meters. This standard is available from the International Electrotechnical Commission.) Additional measuring parameters are Range: 40-100 dB; Exchange Rate: 3 dB; Time Constant: fast; Threshold: Off; and Peak Weighting: C.

Always Maxi Pads sold in the United States by The Procter & Gamble Company (Cincinnati, Ohio), bonded in a tri-fold configuration, with release paper and outer plastic wrapper are modified to make the Examples sound pressure level measurements. The outer wrapper and release paper of the commercial pads were replaced with a test film having an embossed seal 16 formed by the process of disclosure. Prior to forming the embossed seal 16, strips of 2" wide duct tape are attached to both the outer plastic wrapper and topsheet of each end of the pad. The tape covers about the last 1" of the pad ends. On each end of the pad, the adhesive sides of the tape strips are attached to each other to create mounting tabs for the tensile pull. Once the duct tape strips are attached to the open pad, the outer wrapper is then bonded back into the tri-fold configuration. The mounting tabs are then clamped into the Intron jaws prior to the peel strength pull.

Figure 4:
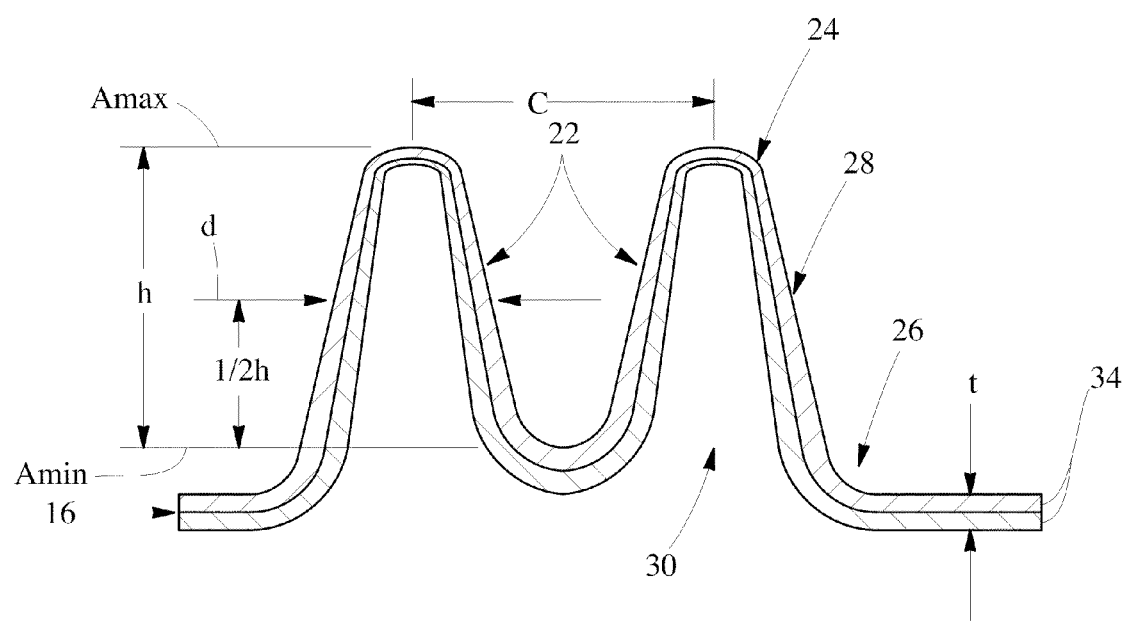
FIG. 4 is a cross-sectional view of a portion of an embossed seal in accordance with an embodiment of the disclosure.
Figure 5:
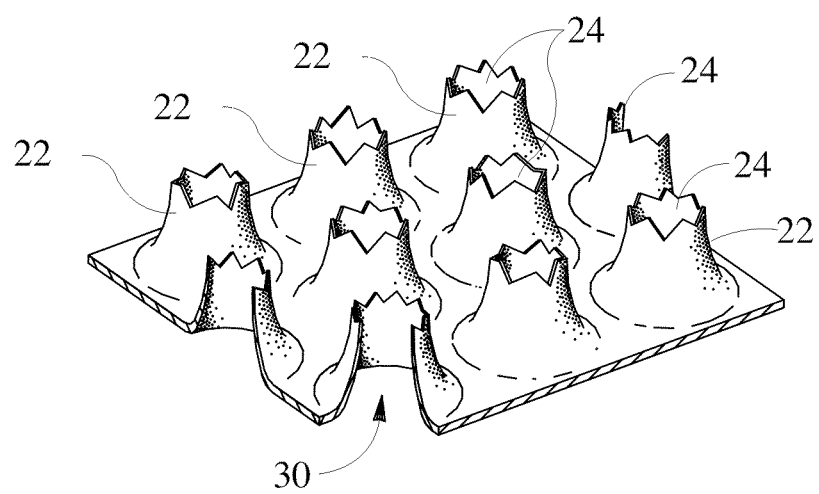
FIG. 5 is a perspective view of a portion of an embossed seal having discrete extended elements with open distal ends in accordance with an embodiment of the disclosure.

The webs are positioned between the forming structure 10 and the pressure source, and a pressure is applied to conform the webs 34 to the discrete forming elements 11 of the forming structure 10. Referring to FIGS. 3A and 3B, an article with an embossed seal 16 having concentric discrete extended elements 22A and 22B is thereby produced. As shown in FIG. 4, the discrete extended elements 22 have open proximal ends 30 and open (as shown in FIG. 5) and or closed (as shown in FIGS. 3A and 3B) distal ends 24.

In one embodiment, the embossed seal 16 resulting from the process described herein can have a structure 10 similar to that described in detail in U.S. Pat. Nos. 7,402,723 or 7,521, 588.

The three-dimensional embossed seal 16 is produced from at least two webs. Each web can be a single layer of web material or a multilayer coextruded or laminate web material as described hereinbefore. Laminate film materials may be coextruded, as is known in the art for making laminate films, including films comprising skin layers.

The discrete extended elements 22 are formed as protruded extensions of each of the webs, generally on a first surface 26 thereof. The discrete extended elements 22 of each of the webs are concentric. Accordingly, the discrete extended element of the outer web may have a diameter slightly larger than the discrete extended element of the inner web, such that the discrete extended element of the inner web resides within the discrete extended element of the outer web, that is, the discrete extended elements are nested. The number, size, and distribution of discrete extended elements 22 on the embossed seal 16 can be predetermined based on desired bond strength, soft feel, and visual effects. It is believed that the high interfacial surface area in intimate contact between the concentric discrete extended elements 22 increases as the height, diameter, aspect ratio, and/or the number of discrete extended elements 22 per unit area increases. It is further believed that an increase in interfacial surface area results in a corresponding increase in bond strength of the embossed seal 16.

Referring to FIG. 4, the discrete extended elements 22 can be described as protruding from a first surface 26 of the embossed seal 16. As such, the discrete extended elements 22 can be described as being integral with the webs, and formed by permanent local plastic deformation of the webs. The discrete extended elements 22 can be described as having a side wall(s) 28 defining an open proximal portion and a closed or open distal end 24. The discrete extended elements 22 each have a height h measured from a minimum amplitude $A_{min}$ between adjacent extended elements 22 to a maximum amplitude $A_{max}$ at the closed or open distal end 24. The discrete extended elements 22 have a diameter d, which for a generally cylindrical structure is the outside diameter at a lateral cross-section. By "lateral" is meant generally parallel to the plane of the first surface 26. For generally columnar discrete extended elements 22 having non-uniform lateral cross-sections, and/or non-cylindrical structures of discrete extended elements 22, diameter d is measured as the average lateral cross-sectional dimension at ½ the height h of the discrete extended element. Thus, for each discrete extended element, an aspect ratio, defined as h/d, can be determined. The discrete extended element can have an aspect ratio h/d of at least about 0.2, at least about 0.3, at least about 0.5, at least about 0.75, at least about 1, at least about 1.5, at least about 2, at least about 2.5, or at least about 3. The discrete extended elements 22 will typically have a height h of at least about 30 microns, at least about 50 microns, at least about 65, at least about 80 microns, at least about 100 microns, at least about 120 microns, at least about 150 microns, or at least about 200 microns. The extended elements 22 will typically be at least the same height as the thickness of the webs, or at least 2 times the thickness of the webs, or preferably at least 3 times the thickness of the webs. The discrete extended elements 22 will typically have a diameter d of about 50 microns to about 5,000 microns, about 50 microns to about 3,000 microns, about 50 microns to about 500 microns, about 65 microns to about 300 microns, or about 75 microns to about 200 microns. For discrete extended elements 22 that have generally non-columnar or irregular shapes, a diameter of the discrete extended element can be defined as two times the radius of gyration of the discrete extended element at ½ height.

For discrete extended elements that have shapes, such as ridges, that extend lengthwise across the entire web material such that the extended elements have a portion of the sidewalls of the extended elements that are open, a diameter of a discrete extended element can be defined as the average minimal width between two opposing sidewalls of the extended element at ½ height.

In general, because the actual height h of any individual discrete extended element can be difficult to determine, and because the actual height may vary, an average height $h_{avg}$ of a plurality of discrete extended elements 22 can be determined by determining an average minimum amplitude $A_{min}$ and an average maximum amplitude $A_{max}$ over a predetermined area of the embossed sea 116. Such average height $hp_{avg}$ will typically fall within the ranges of heights described above. Likewise, for varying cross-sectional dimensions, an average diameter $d_{avg}$ can be determined for a plurality of discrete extended elements 22. Such average diameter $d_{avg}$ will typically fall within the ranges of diameters described above. Such amplitude and other dimensional measurements can be made by any method known in the art, such as by computer aided scanning microscopy and data processing. Therefore, an average aspect ratio $AR_{avg}$ of the discrete extended elements 22 for a predetermined portion of the embossed seal 16 can be expressed as $h_{avg}/d_{avg}$.

In one embodiment, the diameter of a discrete extended element is constant or decreases with increasing amplitude (amplitude increases to a maximum at closed or open distal end 24). The diameter, or average lateral cross-sectional dimension, of the discrete extended elements 22 can be a maximum at proximal portion and the lateral cross-sectional dimension steadily decreases to distal end. This structure 10 is believed to be desirable to help ensure the embossed seal 16 can be readily removed from the forming structure 10. In another embodiment, the diameter of the discrete extended elements 22 increases with increasing amplitude. For example, the discrete extended elements 22 can have a mushroom shape.

Thinning of the webs can occur due to the relatively deep drawing required to form high aspect ratio discrete extended elements 22. For example, thinning can be observed at or near the closed or open distal ends 24 and/or along the sidewalls of the discrete extended elements. By "observed" is meant that the thinning is distinct when viewed in magnified cross-section. Such thinning can be beneficial as the thinned portions offer little resistance to compression or shear when touched. For example, when a person touches the embossed seal 16 on the side exhibiting discrete extended elements 22, the fingertips of the person first contact the closed or open distal ends 24 of the discrete extended elements 22. Due to the high aspect ratio of the discrete extended elements 22, and the wall thinning of the webs at or near the distal ends 24 and/or the sidewalls, the discrete extended elements 22 offer little resistance to the compression or shear imposed on the embossed seal 16 by the person's fingers. This lack of resistance is registered as a feeling of softness, much like the feeling of a velour fabric.

Thinning of the webs at or near the closed or open distal ends 24 and/or sidewalls can be measured relative to the thickness of the webs prior to embossing or relative to the thickness of the land area that completely surrounds the discrete extended elements 22 of the embossed seal 16. The webs will typically exhibit thinning of at least about 25%, at least about 50%, or at least about 75% relative to the thickness of the webs. The webs will typically exhibit thinning of at least about 25%, at least about 50%, or at least about 75% relative to the thickness of the land area surrounding the discrete extended elements 22 of the embossed seal 16.

It should be noted that a fluid impermeable web having only the discrete extended elements 22 as disclosed herein, and not having macroscopic apertures 12 or discrete extended elements 22 having open distal ends 24, can offer softness for any application in which fluid permeability is not required. Thus, in one embodiment, the article includes an embossed seal 16 exhibiting a soft and silky tactile impression on at least one surface thereof, the silky feeling surface of the embossed seal 16 exhibiting a pattern of concentric discrete extended elements 22, each of the discrete extended elements 22 being a protruded extension of the web surfaces and having side walls defining an open proximal portion and a closed or open distal end 24. In certain embodiments, the discrete extended elements 22 have a maximum lateral cross-sectional dimension at or near the open proximal portion.

The "area density" of the discrete extended elements 22, which is the number of discrete extended elements 22 per unit area of first surface 26, can be optimized and the embossed seal 16 will typically include about 4 to about 10,000, about 10 to about 10,000, about 95 to about 10,000, about 240 to about 10,000, about 350 to about 10,000, about 500 to about 5,000, or about 700 to about 3,000 discrete extended elements 22 per square centimeter. In general, the center-to-center spacing can be optimized for adequate tactile impression, while at the same time minimizing entrapment of materials, such as fluids, between discrete extended elements 22. The center-to-center spacing between adjacent discrete extended elements 22 can be about 100 microns to about 5,000 microns, about 100 microns to about 1,000 microns, about 30 microns to about 800 microns, about 150 microns to about 600 microns, or about 180 microns to about 500 microns.

Process for Making Embossed Seal

The process for forming an embossed seal 16 includes feeding the at least two webs between the pressure source and the forming structure 10 and applying a pressure from the pressure source against the webs and the forming structure 10 sufficient to conform portions of the webs to the discrete forming elements 11 of the forming structure 10 to thereby form an embossed seal 16 having concentric discrete extended elements 22. The conformation of the webs to the forming structure 10 can be partial conformation, substantial conformation, or complete conformation, depending upon the pressure generated and the topography of the forming structure 10. While not being bound by theory, it is believed that open distal ends 24 can be formed by locally rupturing the webs while conforming the webs to the discrete forming elements 11 of the forming structure 10.

To obtain permanent deformation of the webs to form the embossed seal 16, the applied pressure is generally sufficient to stretch the webs beyond their yield point.

The process can be a batch process or a continuous process. A batch process can involve providing individual sheets of the at least two web materials placed between the forming structure 10 and pressure source.

A continuous process can involve providing rolls of the at least two web materials that are unwound and fed between the forming structure 10 and pressure source. The at least two web materials can also be provided on a single roll. The forming structure 10 can be, for example, in the form of a roll. As the webs 34 pass between the forming structure 10 roll and the pressure source, an embossed seal 16 is formed. If the pressure source is a compliant substrate 44, the compliant substrate 44 can also be in the form of a roll.

The process can have relatively short dwell times. As used herein, the term "dwell time" refers to the amount of time pressure is applied to a given portion of the webs, usually the amount of time a given portion of the webs spends positioned between the forming structure 10 and pressure source. The pressure is typically applied to the webs for a dwell time of less than about 5 seconds, less than about 1 second, less than about 0.5 second, less than about 0.1 second, less than about 0.01 second, or less than about 0.005 second. For example, the dwell time can be about 0.5 milliseconds to about 50 milliseconds. Even with such relatively short dwell times, embossed seals can be produced with desirable structural features described herein. As a result, the process of the disclosure enables high speed production of embossed seals.

The webs can be fed between the forming structure 10 and the pressure source at a rate of at least about 0.01 meters per second, at least about 1 meter per second, at least about 5 meters per second, or at least about 10 meters per second. Other suitable rates include, for example, at least about 0.01, 0.05, 0.1, 0.5, 1, 2, 3, 4, 5, 6, 7, 8, 9, or 10 meters per second.

Depending upon factors such as the shape of the discrete extended elements 22 on the forming structure 10 and the pressure applied, the distal ends 24 of the extended elements 22 of the embossed seal 16 produced can be either closed or open.

The process can be carried out at ambient temperature, meaning that no heat is intentionally applied to the forming structure 10, the pressure source, and/or webs. It should be recognized, however, that heat can be generated due to the pressure between the forming structure 10 and the pressure source, especially in a continuous process. As a result, the forming structure 10 and/or the pressure source may be cooled in order to maintain the process conditions at the desired temperature, such as ambient temperature.

The process can also be carried out with the webs having an elevated temperature. For example, the temperature of the webs can be less than the melting point of the webs. For example, the temperature of the webs can be at least about 10° C. below the melting point of the webs. The webs, can have a temperature during the process of about 10° C. to about 200° C., about 10° C. to about 120° C., about 20° C. to about 110° C., about 10° C. to about 80° C., or about 10° C. to about 40° C. The webs can be heated during the process by heating the webs, using a heated pressure source, for example a heated fluid pressure source for a static pressure plenum 36 or a heated compliant substrate 44, and/or by heating the forming structure 10. For example, a heated gas can be used as the pressure source for the static pressure plenum 36.

In one embodiment, the precursor web is not heated before being provided between the forming structure and the compliant substrate. In another embodiment, the precursor web, the forming structure and the compliant substrate are not heated before providing the precursor web between the forming structure and the compliant substrate.

In general, the process of the present invention can be carried out at a temperature of from about 10° C. to about 200° C., from about 10° C. to about 120° C., from about 10° C. to about 80° C., or from about 10° C. to about 40° C. The temperature can be measured by, for example, a non-contact thermometer, such as an infrared thermometer or a laser thermometer, measuring the temperature at the nip between the pressure source and forming structure 10. The temperature can also be determined using temperature sensitive material such as Thermolabel available from Paper Thermometer Company.

An average pressure is provided by the pressure source. The average pressure is sufficient to force the webs, which is positioned between the forming structure 10 and pressure source, to conform to the discrete forming elements 11 of the forming structure 10 to form an embossed seal 16. In general, the average pressure provided between the forming structure 10 and static pressure plenum 36 or by a velocity pressure source is about 0.1 MPa to about 25 MPa, about 0.5 MPa to about 20 MPa, about 0.7 MPa to about 10 MPa, about 1 MPa to about 7 MPa, about 1 MPa to about 20 MPa, about 0.5 MPa to about 10 MPa, about 10 MPa to about 25 MPa, or about 0.5 MPa to about 5 MPa. In general, the average pressure provided between the forming structure 10 and a compliant substrate 44 is about 1 MPa to about 100 MPa, about 5 MPa to about 70 MPa, about 10 MPa to about 60 MPa, or about 20 MPa to about 40 MPa. For example, the applied pressure can be up to about 30 MPa.

When a compliant substrate 44 is used as the pressure source, the forming structure 10 and compliant substrate 44 are impressed to a desired compression distance by applying a force to the forming structure 10 and/or compliant substrate 44. The "compression distance" is determined by measuring the distance the forming structure 10 is pressed into the compliant substrate 44. This distance can be measured by bringing the forming structure 10 and compliant substrate 44 into initial contact and then forcing the forming structure 10 and compliant substrate 44 together. The distance that the forming structure 10 and compliant substrate 44 are moved relative to each other subsequent to the initial contact is referred to as the "compression distance." If the forming structure 10 and compliant substrate 44 are both rolls, the compression distance can be measured as the change in distance between the rotational axis of the forming structure 10 and the rotational axis of the compliant substrate 44 due to the force applied after initial contact.

The compression distance of the forming structure 10 and the compliant substrate 44 will typically be from about 0.1 mm to about 5 mm, from about 0.2 mm to about 4 mm, or from about 0.3 mm to about 3 mm.

The process can optionally further include applying a slip agent to the webs and/or the forming structure 10 before the webs are provided between the forming structure 10 and the pressure source. This can be beneficial, especially in a continuous process, to reduce friction between the webs and the forming structure 10. Non-limiting examples of suitable slip agents include silicone, talc, lubricating oils, and the like.

The process can optionally be combined with other processes to further manipulate the webs having the embossed seal 16. In one embodiment, such additional processes can be combined with the process on the same process manufacturing line to produce, for example, packaging for absorbent articles.

The process can further include applying pressure from a second pressure source. The second pressure source can be the same or different than the first pressure source and can be selected from the group consisting of a static liquid pressure plenum, a static gas pressure plenum, a velocity gas pressure source, such as an air knife, a velocity liquid pressure source, such as is used in conventional hydroforming process, and a compliant substrate 44. The pressures exerted on the webs by the second pressure source will typically be similar to those pressures exerted on the webs 34 by the first pressure source described hereinbefore. For example, the process can include using multiple static pressure plenums. In one embodiment, at least two static pressure plenums are provided and pressure is applied on a first portion of the webs 34 between the forming structure 10 and a first static pressure plenum. Pressure can then be applied on the first portion of the webs 34 between the forming structure 10 and a second static pressure plenum to further conform the first portion of the webs 34 to the same protruded elements, apertures, or depressions of the same forming structure 10. This can allow for enhancement of the discrete extended elements 22 formed by the process.

Uses of Articles

The articles can be utilized in a number of different ways, including as packaging materials of absorbent articles, packaging (such as flow wrap, shrink wrap, or polybags), trash bags, food wrap, dental floss, wipes, electronic components, wall paper, clothing, aprons, window coverings, placemats, book covers, and the like.

EXAMPLES

Example 1

Figure 8:
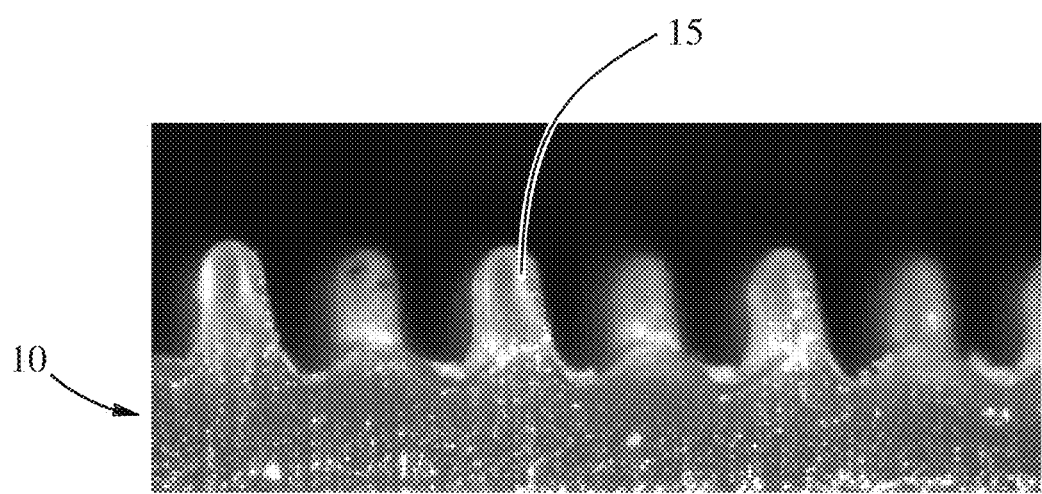

An article having an embossed seal 16 is formed using two webs. The first web is an iridescent film, Aurora Special Effect Film Fluoridescent TM Groovey Green FG 8601 RG-56, obtained from Engelhard Corporation (Iselin, N.J.). The second web is a three layer, coextruded web having 80% LLDPE and 20% LDPE. The embossing process is performed at room temperature. The forming structure 10 includes a plurality of protruded elements. The discrete protruded elements are generally columnar with a circular cross sectional shape. The sidewalls of the discrete protruded elements have a small degree of inward taper. The distal ends of the protruded elements have relatively rounded points. The protruded elements have a height of about 192 microns and are arranged in a hexagonal array with about 254 microns center-to-center spacing. A high magnification side view of the forming structure 10 is shown in FIG. 8.

The pressure source is a compliant substrate 44 having a compliant material 46 in the form of a 6.4 mm thick sheet of 40 durometer gum rubber. The two webs are fed between the forming structure 10 and the compliant substrate 44 and a pressure of about 15 MPa (2,200 psi) is applied to conform the webs to the protruded elements 15 of the forming structure 10, thereby forming an embossed seal 16 having concentric discrete extended elements 22. FIGS. 3A and 3B illustrate the formed embossed seal 16.

Example 2

An article having an embossed seal 16 is formed using two polyethylene films obtained from RKW US, Inc. that are each about 15 microns thick with a basis weight of 14.2 grams per square meter ("gsm"). A compliant substrate of 7 mm thick HYPALON® Rubber (HYPALON CHECKMATE HGS-HT obtained from Perma-Flex Roller Technology, Salisbury, N.C.) is used in the process. The compliant substrate is a two layer laminate made of a 4 mm thick HYPALON® sheet with a Shore A hardness of about 53 and a 3 mm thick HYPALON® sheet with a Shore A hardness of 85. The compliant substrate is in the form of a sheet 15 mm×15 mm square. The 4 mm thick HYPALON® (Shore A hardness of 53) portion of the laminate is in contact with the web during the embossing process. The forming structure is about 1 mm thick metal and had 0.18 diameter depressions spaced 0.25 mm center to center in a hexagonal array. The depressions have circular cross-sections with straight sidewalls. The depressions are vented by including an opening in the bottom surface of the depression to allow the air to escape from the back side during the embossing process. The embossing process is performed using a high speed research press at room temperature. The high speed research press is described in detail in U.S. Patent Application Publication No. 2009/0120308 A1, and is designed to simulate a continuous production line process forming the embossed seal 16. The press is operated to simulate compliant substrate and forming structure roll diameters of 205 mm. The webs are fed between the forming structure 10 and the compliant substrate at a simulated rate of about 6 m/sec.

The compression distance between the compliant substrate and the forming structure, the applied pressure, and force along with the average height of the discrete extended elements 22 of the embossed seal is shown in the table below.

|  | Compression Distance (mm) | Average Discrete Extended Element Height (microns) | Applied Pressure (MPa) | Force (N) |
|---|---|---|---|---|
| Sample 1 | 2.8 | 80 | 27.6 | 6200 |
| Sample 2 | 3.0 | 90 | 31.1 | 7000 |
| Sample 3 | 3.2 | 102 | 38.7 | 8700 |
| Sample 4 | 3.4 | 118 | 46.7 | 10500 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

When a technical feature is disclosed herein in relation to one embodiment, this feature can be combined with any other feature(s) disclosed in other embodiment(s) or claim(s), unless stated otherwise.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An article, comprising:
   at least two webs comprising a first polymeric film and second polymeric film, and a temporary and separable embossed seal joining a portion of the at least two webs, the embossed seal comprising co-formed concentric discrete extended elements surrounded by lands formed in the first polymeric film and the second polymeric film, the discrete extended elements having open proximal ends and portions of the discrete extended elements having a thickness less than that of the lands, wherein an area density of the discrete extended elements of the embossed seal is about 240 to about 10,000 discrete extended elements per square centimeter, wherein the embossed seal is free of adhesives, wherein the concentric discrete extended elements have not been fused together by melting, and wherein at least a portion of the embossed comprises a gap between the first polymeric film and the second polymeric film such that the distal ends of some of the discrete extended elements from one of the first polymeric film and the second polymeric film extend only partially into corresponding discrete extended elements from the other of the first polymeric film and the second polymeric film.

2. The article of claim 1, wherein distal ends and/or sidewalls of the discrete extended elements are thinned by at least about 25% relative to the lands.

3. The article of claim 1, wherein the discrete extended elements have a height at least substantially equal to a thickness of the web.

4. The article of claim 1, wherein the discrete extended elements have closed distal ends.

5. The article of claim 1, wherein each web has a thickness of about 5 microns to about 150 microns.

6. The article of claim 1, wherein the discrete extended elements have an aspect ratio of at least about 0.2.

7. The article of claim 1, wherein the discrete extended elements have a diameter of less than about 5,000 microns.

8. The article of claim 1, further comprising an unsealed portion disposed adjacent to the embossed seal, the unsealed portion comprising portions of the at least two webs that are substantially free of concentric discrete extended elements.

9. The article of claim 8, wherein the embossed seal is disposed along opposing sides of the at least two webs and the unsealed portion is disposed between the opposing sides having the embossed seal.

10. The article of claim 1, wherein the first polymeric film is the same as the second polymeric film.

11. The article of claim 1, wherein the first polymeric film is different from the second polymeric film.

* * * * *